United States Patent [19]

Bryan et al.

[11] Patent Number: 4,900,422

[45] Date of Patent: Feb. 13, 1990

[54] SYSTEM FOR MONITORING AND REPORTING THE OPERABILITY AND CALIBRATION STATUS OF A DISSOLVED OXYGEN SENSOR

[76] Inventors: Avron I. Bryan, 26 Country Club Rd., Cocoa Beach, Fla. 32931; Michael R. Cushman, 521 Brandonwood Rd., Kingsport, Tenn. 37662

[21] Appl. No.: 215,784

[22] Filed: Jul. 5, 1988

[51] Int. Cl.$^4$ ............................................. G01N 27/46
[52] U.S. Cl. ...................................... 204/401; 204/1 T; 204/412; 204/415
[58] Field of Search ............... 204/1 P, 401, 415, 412, 204/435

[56] References Cited

U.S. PATENT DOCUMENTS

| | | | |
|---|---|---|---|
| 3,661,748 | 5/1972 | Blackmer | 204/401 |
| 3,718,568 | 2/1973 | Neuwelt | 204/401 |
| 4,168,220 | 9/1979 | McAdam et al. | 204/401 |
| 4,189,367 | 2/1980 | Connery et al. | 204/419 |
| 4,541,901 | 9/1985 | Parker et al. | 204/402 |

Primary Examiner—T. Tung
Attorney, Agent, or Firm—Macdonald J. Wiggins

[57] ABSTRACT

A system for real time, on-line dissolved oxygen (DO) measurement of a process solution provides continuous data of the physical condition of the DO sensor and of the entire system performance. A DO sensor is disposed in the solution with two external electrodes adjacent thereto. A time-varying low level signal is applied to one electrode producing a current through the sensor membrane and grounded electrode, which is detected by a cross-correlation circuit to monitor the membrane impedance. The other electrode is periodically driven by a short, low level dc pulse, producing electrolysis of the water between the two electrodes, and generating a small, repeatable amount of oxygen ions. The sensor response is analyzed providing a direct indication of the sensor and system performance.

17 Claims, 2 Drawing Sheets

SYSTEM FOR MONITORING AND REPORTING THE OPERABILITY AND CALIBRATION STATUS OF A DISSOLVED OXYGEN SENSOR

This application is related to pending U.S. application Ser. No. 058,866, filed June 5, 1987, now U.S. Pat. No. 4,822,456.

1. Field of the Invention

The present invention relates to a dissolved oxygen concentration monitoring system for a solution containing water, and more particularly to a system including monitoring of the physical condition of an oxygen sensor of the system.

2. Description of the Prior Art

The concentration of oxygen in processes containing water is important in many industrial processes and is critical for processes based on oxygen-using microorganisms; for example, fermentation, recombinant DNA processes, and waste water treatment. The present real time measurement of oxygen in industrial processes utilizes two forms of sensors: galvanic (voltage); and amperometric (current). The oxygen concentration signal developed by the sensor is in response to the partial pressure of gases in the solution and the diffusion of oxygen ions across the membrane. Specifically, oxygen ions are reduced at the cathode in the sensor, generating either a potential or current. In either type sensor, the operation of the sensor is maintained at a state in which the signal from the sensor is essentially linearly proportional to the partial pressure of oxygen in the solution compared to oxygen in the air.

There are a number of problems that can occur with this measurement system. For example, the membrane can become coated by the process or can change due to structural failure, such as cracks, leakage or degradation. In the sensor body, the physical condition of the electrodes and the condition of the electrolyte directly affect the sensor signal current. These problems can occur in prior art systems without being detected resulting in out-of-tolerance processes. Such failures can produce significant losses in time and money. There are no systems known that continuously detect changes in the sensor membrane and periodically detect performance changes in the sensor or system.

Thus, there is a need for a dissolved oxygen sensor system in which defects in the oxygen sensor can be detected in real time while a process is on-line, thereby reducing the probability of undetected failures and catastrophic results.

SUMMARY OF THE INVENTION

The present invention is a dissolved oxygen measurement system having a unique real time, on-line capability for continuously monitoring the dissolved oxygen sensor membrane impedance, and for testing the sensor and the system response to oxygen by generating in the process solution a known value of additional oxygen in the vicinity of the sensor. The system generates reports on relative changes in the impedance of the sensor membrane since the last calibration, and relative changes of the sensor response to the controlled quantity of additional oxygen in the process solution since the last calibration.

A novel oxygen sensor is provided having two electrodes external to the body of a standard amperometric or galvanic dissolved oxygen sensor. When the system is in use, the oxygen sensor and the two additional external electrodes are disposed in the process solution or stream. The two additional electrodes function as an anode and a cathode. A small current is passed from anode to cathode through the solution. The resulting electrolytic action produces a small amount of extra oxygen. The anode is placed such that the oxygen thus generated will reach the sensor.

The measurement system is controlled by a computer with appropriate algorithms and additional control hardware to perform all of the functions of oxygen measurement, testing and analysis of the sensor and system response. To this end, the signal from the oxygen sensor is applied to an analog-to-digital (A/D) converter and the digitized signals are input to the computer. The computer processes the signals and converts the results to operate numerical read-outs of the oxygen concentration being measured.

It is preferred to include a temperature sensor in the process on-line near the oxygen sensor. The output of the temperature sensor is converted to digital form which is used by the system computer to compensate nonlinearities in oxygen sensor concentration readings.

A low level voltage pseudorandom binary signal is applied by the system to the impedance anode electrode which produces a current through the sensor membrane. The applied binary signal is less than 0.2 millivolts and its effect is easily removed from the dc current or voltage signal produced by the sensor. A current from the test signal will flow from the impedance anode electrode through the process solution, through the membrane, through the sensor electrolyte and reference electrode to a measurement element in the system.

As may now be understood, the pseudorandom test current will be flowing in the sensor cathode electrode output along with the dc currents generated by the reduction of the oxygen in the process. The binary test currents will add and subtract from the dc oxygen signal currents. The composite signal is applied via the A/D converter to the system computer which cross-correlates the composite signal with the known pseudorandom signal and extracts a value proportional to the impedance of the membrane. This impedance can range from several thousand ohms to several megohms as normal operating values. Other impedances in the signal path of the test signal are normally less than 0.1% of the lowest membrane impedance and therefore may be ignored.

There are certain capacitances involved in the external electrodes, sensor membrane and internal electrodes, and process solutions; therefore, the pseudorandom signal is produced at a low bit rate such as 1 bit per second to eliminate any effect of the capacitances. The measurements will thus provide the resistive component of the sensor membrane.

Periodic generation of an oxygen signal to test and verify the entire measurement system is provided by the system controlled generator and the two external electrodes. The system, on a programmable periodic basis, applies a low level current or potential signal from the Y electrode through the process solution to the external anode electrode. The external cathode electrode returns the drive signal to the measurement system ground. The test current results in the electrolysis of the process solution in which the $H_2O$ molecules produce a repeatable quantity of hydrogen and oxygen gases. The hydrogen gas is exhausted by the process system and is ignored by the oxygen sensor. The additional oxygen value (over the process solution average concentration of oxygen) is monitored in the normal manner. The system oxygen estimate delivered to users and control systems is maintained at the last average reading before the application of the test signal. The effect of the additional generated oxygen on the sensor is monitored and compared with past behavior for system check purposes, but is not reported as additional dissolved oxygen in the solution process.

The system computer, having issued the test signal for oxygen, can now subtract the additional oxygen level signal from the normal level of oxygen in the process solution. System computer algorithms then compare the amplitude response, initial speed of response, and decay response to the additional oxygen to detect both sensor and system performance.

At the time of calibration of the system, the initial membrane impedance, temperature and the system response to the additional oxygen test signal are measured and stored. Thereafter the stored values are used as references to compare against the continuous membrane test results and the sensor additional oxygen test results. Changes in the membrane (after correction for temperature) values indicate degradation or failure of the sensor. Internal sensor electrode degradation or change in electrolyte is indicated by the time and shape of the response to the additional oxygen test. A failure in some other part of the system is indicated by a lack of response to the known additional oxygen. The measurement system will report on the need for calibration or warnings that the sensor or system have failed or the performance thereof has degraded.

In some process solutions, the presence of oxygen is harmful (e.g., electrical generation systems) and oxygen sensors are used only to detect the presence of any oxygen. In these cases, only the membrane test process is required.

DETAILED DESCRIPTION OF THE PREFERRED EMBODIMENT

Figure 1:
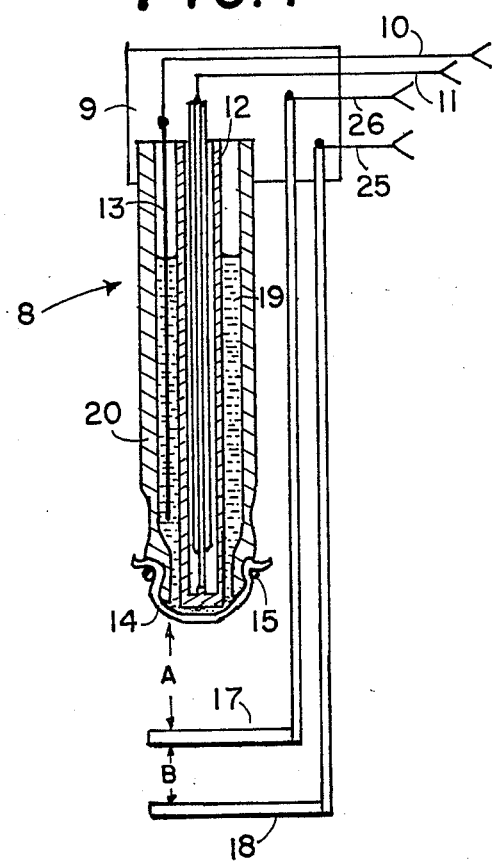
FIG. 1 is a cross sectional view of an oxygen sensor with external test and monitor electrodes in accordance with the invention.

The invention is a system for monitoring for dissolved oxygen in a process solution. A dissolved oxygen sensor is combined with two test electrodes in the process solution to provide means for testing, analyzing, and reporting the oxygen sensor status as well as the total system response. Referring to FIG. 1, a standard dissolved oxygen sensor 8 is mounted to a bracket 9 from which monitor and test electrodes 17 and 18 depend. The dissolved oxygen sensor may be an amperometric or galvanic type. The anode electrode 13 of sensor 8 is preferably formed from silver and is immersed in an electrolyte 19 saturated with silver chloride. The cathode electrode 12 is preferably formed from platinum. Electrodes 13 and 12 are disposed in a housing 20 having an open lower end. A sensor membrane 14 is formed from Teflon$^R$ covering the open end of housing 20, and is held in place by a rubber "O" ring 15. Test electrode 17 functions as a cathode electrode and is spaced a distance A from membrane 14. Test electrode 18 functions as an anode electrode and is spaced a distance B from test electrode 17. Distances A and B are not critical but are normally less than 0.5 inches. Test electrode 17 can be of any suitable cathode material, such as gold or platinum. Test electrode 18 should be formed of material that has a low oxygen overpotential such as platinum or lead dioxide.

As will be noted, anode electrode 13 of sensor 8 is connected to lead 10, and cathode electrode 12 connects to lead 11. Test electrode 17 is connected to lead 26, and test electrode 18 connects to lead 25.

Figure 2:
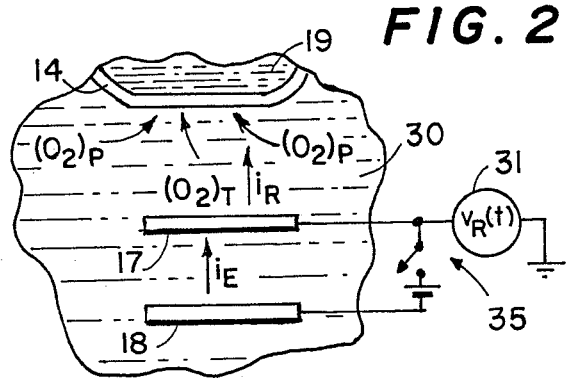
FIG. 2 is a partial view of the sensor and electrodes of FIG. 1 illustrating generation of a pulse of excess oxygen ions for test purposes.

Turning now to FIG. 2, a portion of an operating system is shown with process solution 30. Membrane 14 is indicated with oxygen ions $(O_2)_p$ incident thereon. The measurement system will normally measure the concentration of such oxygen ions in solution 30. As will be described in more detail below, a very low amplitude time varying voltage $v_R(t)$ 31 is applied between ground and test electrode 17. A small current $i_R$ will flow through membrane 14 to cathode electrode 13 (not shown) and will be proportional to the impedance of membrane 14. Suitable instrumentation, as described hereinafter, will measure this impedance. As will be described below, real time monitoring of this impedance permits an alarm if any change in membrane impedance occurs during operation due to contamination or physical damage.

Figure 3:
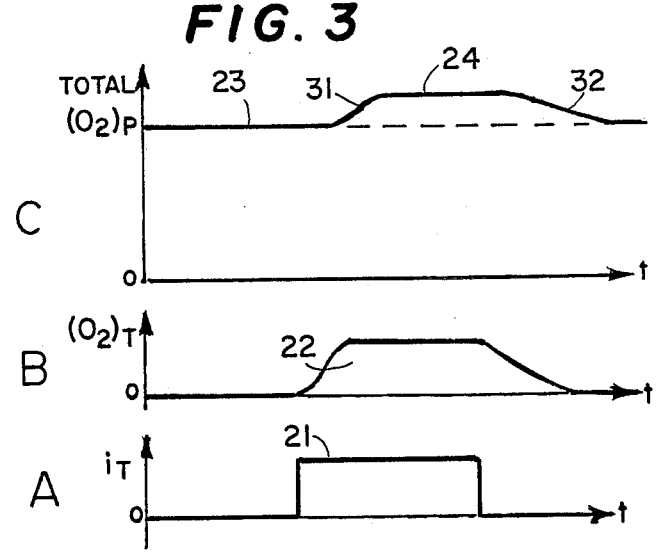
FIG. 3 is a set of waveforms produced in generation of an oxygen ion pulse.

The condition of the electrodes 12, 13 and electrolyte 19 is monitored by periodically producing a very small increase in oxygen concentration directly at the sensor membrane 14. A voltage source $V_E$ and switch means 35 is connected between electrodes 17 and 18. The voltage is applied in a short interval ($t_1$ to $t_2$) as indicated in line A the waveform diagram of FIG. 3. An electrolysis current $I_E$ will flow, causing electrolysis of the water in solution 30. The oxygen $(O_2)_T$ released will, as indicated in line B, cause an increase in total $(O_2)_p$ as shown in line C. When voltage $V_E$ is turned off at $t_2$, the excess oxygen will be dispersed by the process.

A small increase in the measured value of total oxygen 23 from sensor 8 will occur. The increase is analyzed for amplitude 24, rise time 31, and decay time 32. The characteristics of the waveform at calibration are stored and subsequent measurements are compared to the calibration. Any physical changes in sensor 8 will affect the sensor's response to the test oxygen pulse and an alarm may be generated if a change is out of preselected thresholds.

Figure 4:
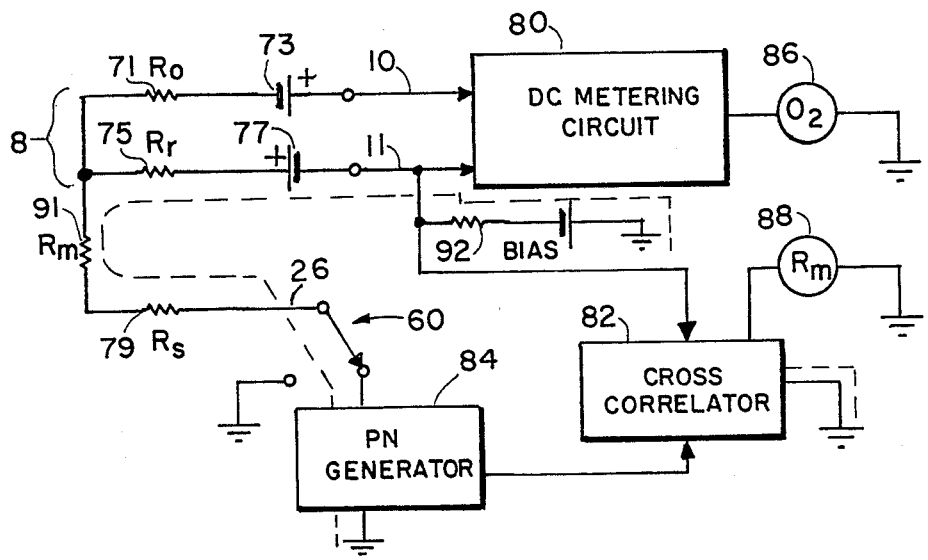
FIG. 4 is an equivalent circuit of a system using the sensor and electrodes of FIG. 1.

The operation of the impedance monitoring system of the invention may best be understood with reference to FIG. 4 in which a simplified functional schematic diagram is shown. The ion electrode 12 of FIG. 1 of oxygen sensor 8 is represented by an equivalent voltage cell 73. The voltage of cell 73 will vary with the concentration of oxygen ions in the process. An equivalent resistance 71 ($R_o$) is the impedance from electrode 12 of FIG. 1 to membrane 14. An equivalent reference voltage cell 77 represents reference electrode 13 of FIG. 1 and its potential is normally constant, although the potential will vary with temperature. The impedance from electrode 13 to membrane 14 is indicated by equivalent resistance 75 ($R_r$).

The reference and ion electrodes are connected by leads 10 and 11 to a dc metering circuit 80 which compares potential 73 to potential 77 and produces a reading on meter 86 calibrated as the concentration of dissolved oxygen in the process solution. In accordance with the invention, contact is made with the process solution by test cathode electrode 17 which is connected by switch 60 to pseudorandom (PN) signal generator 84 by lead 26. An equivalent solution resistance 79 ($R_S$) is shown which occurs between electrode 17 and membrane 14. An equivalent membrane resistance $R_M$ 91 is shown between the solution resistance $R_S$ 79 and the common point to equivalent resistances $R_r$ 75 and $R_o$ 71. The membrane resistance $R_M$ 91 is at least 10,000 times greater than the sum of $R_S$ and $R_r$ or $R_S$ and $R_o$.

Although not shown, the impedances generally include small capacitances. These do not affect the dc measurement and the PN signal is generated at a low rate, for example, 1 bit per second. Thus, the capacitive reactance is negligible.

The level of the PN signal is low, on the order of 0.2 millivolts and is thus negligible with respect to the biased dc voltage and dc signal voltages which are typically hundreds of millivolts. Therefore, it has no effect on the oxygen concentration measurement. As will now be recognized, a test current $i_R$ proportional to values of $R_M$ will flow to ground through the bias resistor 92. The waveform from PN generator 84 provides the reference to cross correlator 82 which extracts the $i_R$ signal and produces a reading on meter 88 proportional to the membrane resistance $R_M$.

Figure 5:
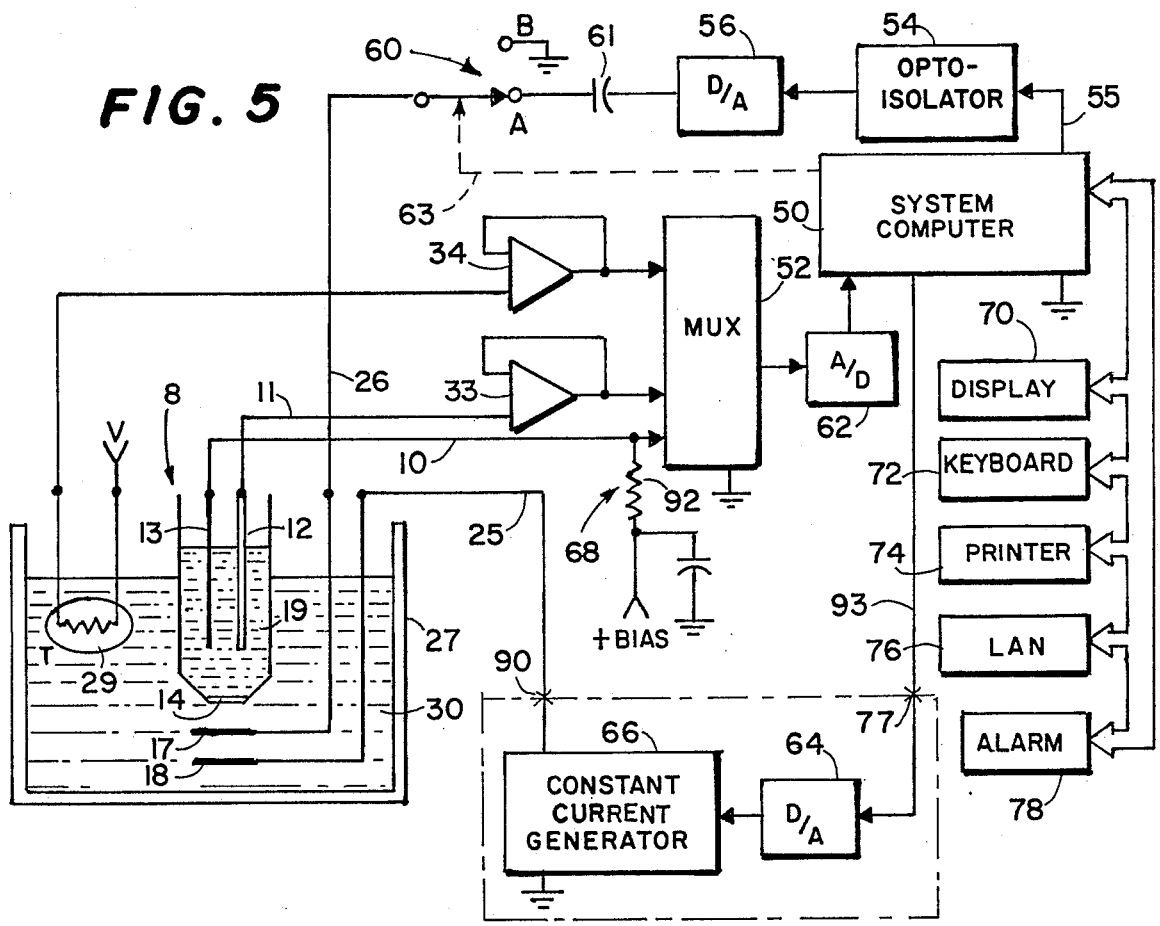
FIG. 5 is a schematic and block diagram of a preferred embodiment of the system of FIG. 4 utilizing a computer for measuring sensor impedance and testing of the sensor with oxygen ion pulses.

The preferred implementation of the invention is shown by the schematic and block diagram of FIG. 5.

A process solution 30 for which the oxygen concentration is to be measured is shown in a tank 27. A dissolved oxygen sensor 8 is shown immersed in the solution 30. In addition, a temperature sensor 29, which may be of any electrical type, is provided to allow automatic temperature compensation of the dissolved oxygen sensor response as well as the estimate of the impedance $R_M$ of sensor membrane 14.

A system computer 50 is provided having a number of stored programs. One program is used to generate a pseudorandom signal. As previously discussed, it is desirable that the pseudorandom signal be bimodal at a low frequency such as 1 bit per second. The pseudorandom signal is produced by the system computer 50 on lead 55 and fed to a digital-to-analog (D/A) converter 56 via an optical isolator 54. A blocking capacitor 61 is used to remove any dc component in the pseudorandom signal. The test signal is connected to test electrode 17 via electronic switch 60 (shown in equivalent form) and lead 26. Switch 60 is commanded via lead 63 to position A for testing sensor membrane 14. When switch 60 is in position A, the PN signal will produce an output on lead 11 superimposed on the dc oxygen concentration signal. For monitoring the condition of sensor 8, pulses of excess oxygen ions are generated as discussed above. Computer 50 commands switch 60 to position B, and a second stored program in the system computer 50 commands a constant current generator 66 via D/A converter 64 to generate an electrolysis current on a programmable periodic basis. Further, the current amplitude and time duration thereof are programmable to accommodate the process solution characteristics and the locations of the test electrode 17 and the electrolysis electrode 18. The current to generate the additional oxygen is applied via lead 25 to the electrolysis electrode 18. Prior to the test signal command to the generator 66, a command on lead 63 to switch 60 to position "B" is issued, thereby providing a return path for the current via test electrode 17.

Having described the test procedures controlled by computer 50, the operation of the system will now be discussed. The oxygen sensor anode 12 dc output is available via lead 11 to the circuit 33 which is connected to be either an emitter follower or a current-to-voltage converter to accommodate the type of dissolved oxygen sensor 8 in use. Circuit 33 drives the multiplexer (MUX) 52. Temperature sensor 29 provides a voltage signal via emitter follower 34 to MUX 52. The potential of the bias voltage via bias network 68 on the sensor cathode lead 10 is connected directly to MUX 52. Multiplexer 52 has its output connected via an analog-to-digital (A/D) converter 62 to system computer 50.

As previously discussed, the voltage levels of the pseudorandom signals applied to the test electrode 17 are on the order of 0.2 millivolts or less while the biased dc voltages and dc signal voltages are on the order of hundreds of millivolts. Therefore, A/D converter 62 necessarily has a capability of 14 bits.

System computer 50 includes stored programs to perform cross-correlation and statistical analyses on the data contained in the dc signal from the oxygen anode electrode 12 and from test and monitoring signals. As is apparent from the equivalent circuit of FIG. 4, PN current $i_R$ will produce a voltage drop across resistor 92 which is connected to ground through the bias source. This voltage is analyzed by the cross-correlation program to produce an output proportional to the impedance $R_M$ of membrane 14. The programs analyze the response of the sensor to the test oxygen pulse 22 of FIG. 3, and measure the solution oxygen concentration. Thresholds for all parameters of the sensor 8, and the test and monitoring elements of the system, are programmable and are entered into system computer 50. Whenever any of the programmed thresholds is exceeded, an appropriate alarm 78 is actuated. The process solution oxygen concentration, the sensor membrane impedance, the sensor response time and decay time, and process temperature are available for real time monitoring on the system display 70, printer 74; a local area network 76; and alarm 78.

Calibration of the system may be carried out by entering appropriate keyboard commands via keyboard 72 or via the local area network 76. The system computer program may select new threshold values for the sensor 8 and system test and monitoring signals based on the calibration.

In some process solutions, dissolved oxygen may be harmful to the process being monitored, and sensor 8 is used to detect the presence of oxygen. The use of electrolysis electrode 18 and current generator 66 are undesirable in such applications. Leads 25 and 93 are broken at points 90 and 77 respectively, disabling the oxygen ion production function and the system used to monitor the membrane impedance $R_M$.

ALTERNATIVE EMBODIMENT

Figure 6:
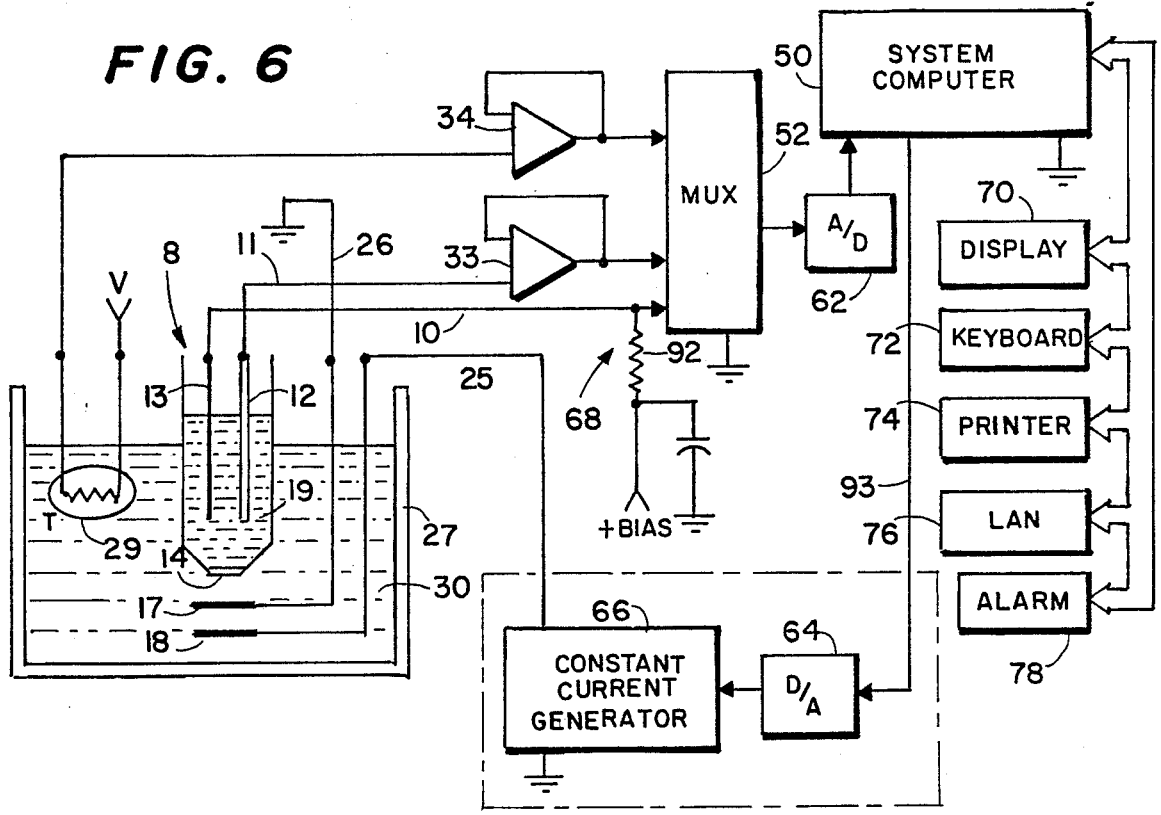
FIG. 6 is an alternative embodiment of the system of FIG. 5 utilizing a computer for testing the sensor with oxygen ion pulses.

The use of electrode 17 for monitoring the impedance of sensor membrane 14 and electrode 18 and 17 for producing oxygen ion pulses for monitoring the internal status of sensor 8 in conjunction with computer 50 has been disclosed above. In an alternative embodiment shown in schematic and block diagram form of FIG. 6, electrode 17 is permanently connected to system ground and computer 50 is programmed to periodically enable constant current generator 66 as previously described. The program includes the following functions:

measures dc levels from sensor electrodes 12 and 13;
determines oxygen ion concentration from dc levels;
displays oxygen ion concentration;
analyzes amplitude, rise time and decay time of dc levels produced by periodic oxygen ion pulses from electrolysis by electrodes 17 and 18;
monitors such amplitude, rise time and decay time of dc levels for any changes therein; and
compares such changes to thresholds and produces alarms when thresholds are exceeded.

With this embodiment, there is no requirement for the program to include a pseudorandum signal generator or cross correlation function.

Although specific illustrations of the preferred embodiment have been presented, these are for exemplary purposes only and various alternative arrangements may be used without departing from the spirit and scope of the invention.

We claim:

1. In a dissolved oxygen measuring system having an oxygen ion sensor disposed in a process solution, said sensor including an oxygen electrode for producing a first dc signal proportional to the oxygen ion concentration in said solution and a reference electrode for producing a dc reference signal, an electrolyte contacting the oxygen electrode and the reference electrode, and a permeable membrane separating the electrolyte from said solution, a test and monitoring subsystem comprising:

(a) an electrode disposed in said process solution adjacent said sensor membrane;
(b) time varying electrical signal generator means for producing a time varying signal, said generator having a first output lead connected to a ground, and a second output lead connected to said electrode, said generator thereby producing a time varying electrical current through said solution, said sensor membrane, said electrolyte, and said reference electrode to said ground, said current producing an output time varying signal proportional to an impedance value of said sensor membrane superimposed on said dc reference signal;
(c) cross-correlation means for cross correlating said time varying current with said output time varying signal and said dc reference signal to separate said output time varying signal therefrom; and
(d) means for measuring the value of said separated output time varying signal, said value thereby being proportional to said membrane impedance.

2. The subsystem as recited in claim 1 in which said time varying signal is a pseudorandom signal.

3. The subsystem as recited in claim 2 in which said time varying signal is a binary signal.

4. The subsystem as recited in claim 3 in which said signal generation means includes a computer programmed to generate said pseudorandom binary signal.

5. The subsystem as recited in claim 4 in which said cross correlation means includes said computer further programmed to cross correlate said pseudorandom binary signal with said output time varying signal superimposed on said dc reference signal.

6. A test and monitoring system for providing on-line, real-time monitoring of the condition of a dissolved oxygen sensor having an oxygen electrode, a reference electrode, an electrolyte contacting the oxygen electrode and the reference electrode, and a permeable membrane separating the electrolyte from a solution, said sensor immersed in a process solution, comprising:

(a) a test electrode immersed in said process solution adjacent said ion sensor membrane;
(b) generator means for generating a low level, time varying signal, an output of said generator connected between a system ground and said test electrode for producing a time varying current through said membrane to said reference electrode, and through a resistor to said system ground;
(c) means for measuring a voltage drop across said resistor from said time varying current and a dc reference current in which a time varying component is proportional to the impedance of said membrane;
(d) an electrolysis electrode immersed in said process solution and spaced apart from said test electrode;
(e) a switch connected between said test electrode and said generator for periodically connecting said test electrode to said system ground;
(f) a source of direct current connected between said electrolysis electrode and said system ground, said source energized when said switch is connected to said system ground for producing electrolysis in said process solution to thereby release a pulse of a predetermined volume of oxygen ions incident on said sensor, said oxygen ions producing a small increase in dissolved oxygen relative to dissolved oxygen due to the process wherein said oxygen ion sensor produces a voltage pulse superimposed on a process oxygen ion level voltage and wherein said voltage pulse has an amplitude much smaller than said oxygen ion level voltage; and
(g) means for comparing the rise time, magnitude, and decay time of said oxygen voltage pulse with calibrated values and for detecting deviations from calibrated values indicative of deterioration of said dissolved oxygen sensor.

7. The system as recited in claim 6 in which said time varying signal is a pseudorandom binary signal.

8. The system as recited in claim 7 which further comprises a system computer.

9. The system as recited in claim 8 in which said generator means includes a first program resident in said computer for generating said pseudorandom binary signal, said voltage drop measuring means is a second program resident in said computer for cross correlating said voltage drop with said pseudorandom binary signal to thereby separate said time varying component, and a third program for measuring and displaying a value of said membrane impedance.

10. The system as recited in claim 9 in which said switch is an electronic switch, and said computer includes means for periodically operating said switch.

11. The system as recited in claim 9 in which said comparing and detecting means includes a fourth program for measuring and storing calibrated values of said rise time, said magnitude, and said decay time and for comparing monitored ones of said oxygen voltage pulses with said calibrated values, and for displaying deviations from such calibrated values.

12. The system as recited in claim 11 in which said fourth program includes thresholds for said calibrated values and means for enabling alarms when a threshold is exceeded.

13. A test and monitoring system for providing on-line, real-time monitoring of the condition of a dissolved oxygen sensor having an oxygen electrode, a reference electrode, an electrolyte contacting the oxygen electrode and the reference electrode, and a permeable membrane separating the electrolyte from a solution, said sensor immersed in a process solution, comprising:

(a) a test electrode immersed in said process solution adjacent said ion sensor membrane;

(b) an electrolysis electrode immersed in said process solution and spaced apart from said test electrode;

(c) a switch connected between said test electrode and said generator for periodically connecting said test electrode to said system ground;

(d) a source of direct current connected between said electrolysis electrode and said system ground, said source energized when said switch is connected to said system ground for producing electrolysis in said process solution to thereby release a pulse of a predetermined volume of oxygen ions incident on said sensor, said oxygen ions producing a small increase in dissolved oxygen relative to dissolved oxygen due to the process wherein said oxygen ion sensor produces a voltage pulse superimposed on a process oxygen ion level voltage and wherein said voltage pulse has an amplitude much smaller than said oxygen ion level voltage; and (e) means for comparing the rise time, magnitude, and decay time of said oxygen voltage pulse with calibrated values thereof, and for detecting deviations from calibrated values indicative of deterioration of said dissolved oxygen sensor.

14. The system as recited in claim 13 which further comprises a system computer.

15. The system as recited in claim 14 in which said switch is an electronic switch, and said computer includes means for periodically operating said switch.

16. The system as recited in claim 13 in which said comparing and detecting means includes a fourth program for measuring and storing calibrated values of said rise time, said magnitude, and said decay time and for comparing monitored ones of said oxygen voltage pulses with said calibrated values and for displaying deviations from such calibrated values.

17. The system as recited in claim 16 in which said program includes thresholds for said calibrated values and means for enabling alarms when a threshold is exceeded.

* * * * *